(12) United States Patent
Okuno

(10) Patent No.: US 9,743,894 B2
(45) Date of Patent: Aug. 29, 2017

(54) MOBILE-TYPE RADIOGRAPHIC IMAGE PICK UP DEVICE

(71) Applicant: SHIMADZU CORPORATION, Kyoto (JP)

(72) Inventor: Tomoharu Okuno, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 70 days.

(21) Appl. No.: 14/784,528

(22) PCT Filed: Apr. 25, 2013

(86) PCT No.: PCT/JP2013/002830
§ 371 (c)(1),
(2) Date: Oct. 14, 2015

(87) PCT Pub. No.: WO2014/174554
PCT Pub. Date: Oct. 30, 2014

(65) Prior Publication Data
US 2016/0058402 A1  Mar. 3, 2016

(51) Int. Cl.
*A61B 6/00* (2006.01)
*B62B 5/04* (2006.01)
(Continued)

(52) U.S. Cl.
CPC ............ *A61B 6/4476* (2013.01); *A61B 6/105* (2013.01); *A61B 6/4405* (2013.01);
(Continued)

(58) Field of Classification Search
CPC ......... A61B 6/105; A61B 6/04; A61B 6/4405; A61B 5/04
See application file for complete search history.

(56) References Cited

U.S. PATENT DOCUMENTS

2012/0155616 A1* 6/2012 Rijken ................ A61B 6/4405
378/198

FOREIGN PATENT DOCUMENTS

JP        9-58462      3/1997
JP        2001-97221   4/2001
(Continued)

OTHER PUBLICATIONS

PCT/JP2013/002830, International Search Report mailed Jun. 4, 2013, 5 pages—Japanese, 2 pages—English.
PCT/JP2013/002830 filed Apr. 25, 2013.

*Primary Examiner* — David J Makiya
*Assistant Examiner* — Dani Fox
(74) *Attorney, Agent, or Firm* — Andrew F. Young, Esq.; Lackenbach Siegel, LLP

(57) ABSTRACT

An improved configuration of a mobile-type radiographic image pickup device reliably stops on a flat path without play. More specifically, the prevent invention stops reliably on an inclined path. Where a carriage accelerates regardless of that fact that a deceleration control unit has begun to restrict the movement of the carriage, a brake control unit causes a brake device to operate. According to the present invention, if the carriage accelerates regardless of the fact that a deceleration control unit has begun to restrict the movement of the carriage, the brake device is promptly operated, and prevents concern regardless of the application of an instruction to stop the carriage which is travelling on an incline, and prevents the carriage from running for a long period to time.

8 Claims, 20 Drawing Sheets

(51) Int. Cl.
*A61B 6/10* (2006.01)
*B62B 5/00* (2006.01)

(52) U.S. Cl.
CPC ............ *A61B 6/4429* (2013.01); *A61B 6/467* (2013.01); *A61B 6/54* (2013.01); *B62B 5/0069* (2013.01); *B62B 5/04* (2013.01)

(56) References Cited

FOREIGN PATENT DOCUMENTS

| | | |
|---|---|---|
| JP | 2001-309910 | 11/2001 |
| JP | 2010-187820 | 9/2010 |
| JP | 2010-213769 | 9/2010 |

* cited by examiner

MOBILE-TYPE RADIOGRAPHIC IMAGE PICK UP DEVICE

CROSS REFERENCE TO RELATED APPLICATIONS

This application relates to and claims priority as a national phase §371 from Ser. No. PCT/JP2013/002830 filed Apr. 25, 2013, the entire contents of which are incorporated herein by reference.

FIGURE SELECTED FOR PUBLICATION

FIG. 1

BACKGROUND OF THE INVENTION

Field of the Invention

The present invention relates to a mobile radiation device having a set of each module required for the radiation imaging installed on a wheeled platform and particularly relates to the mobile radiation device having a power assist function.

Technical Background

Conventionally, the mobile radiation device used in the medical facility is a device having a set of each module required for the radiation imaging on the electrically movable wheeled platform. Typical modules installed to the wheeled platform are a radiation source that radiates radiation, a detection means that detects the transmissive radiation through the subject, and an image generation means that images the detected signals output from the detection means (refer to Patent Document 1, Patent Document 3, Patent Document 3).

Each module constitutes such mobile radiation device is installed on the handcart wheeled platform. When the operator needs to move the imaging device, the operator should push the wheeled platform to move. Despite a handcart type, each installed module is relatively heavy so that the wheeled platform has a power assist function.

Specifically, according to the conventional mobile radiation device, when the operator grips the bar installed to the wheeled platform and pushes, the wheeled platform senses the pressure to the bar so that the wheeled platform per se automatically moves according to the pressure. According to such structure, the operator can move the mobile radiation device with the sense as if operating the empty and light wheeled platform without a heavy load.

When the operator is moving the device by gripping the bar and tries to stop the move of the device, the operator operates a brake lever attached to the bar. When the brake lever is operated, the brake module installed to wheels of the wheeled platform becomes operative. The brake module is e.g., a drum brake that is operative to brake the rotation of the wheel by e.g., friction of the brake shoe. However, in such structure, the braking is too strong and the wheeled platform will jounce greatly. The procedural improvement relative to braking so as to control the jounce has been conventionally developed. Specifically, even when the operator turns the brake lever on, the brake module would not be immediately operative.

It is necessary to lower the velocity of the wheeled platform to some extent prior to turning the brake module operative to control the jounce due to braking. Specifically, when the operator operates the brake lever to stop the mobile radiation device, it must be controlled that the rotation of wheels of the wheeled platform firstly should be slowed down without turning the brake module operative. Such control can be achieved by controlling the motor driving wheels. And when the velocity of the wheeled platform is slowed down satisfactorily, the above brake module is turned operative. In such mode, the wheeled platform is realistically stopped through two steps including lowering the velocity with the motor control and braking with the brake module so that the mobile radiation device that does not jounce when stopping can be provided.

Accordingly, there is a need for an improved mobile-type radiographic image pickup device, and method and system for operating the same.

PRIOR ART DOCUMENTS

Patent Documents, the entire content of which is incorporated herein.
Patent Document 1: JP Patent Published 2001-309910
Patent Document 2: JP Patent Published 2010-187820
Patent Document 3: JP Patent Published 2010-213769

ASPECTS AND SUMMARY OF THE INVENTION

Problems to be Solved by the Invention

However, there are following problems in the conventional mobile radiation device. Specifically, the conventional mobile radiation device has not been under consideration of the case in which the brake is turned on while moving on the slope.

For example, it is considered the case of that the operator tries to stop the mobile radiation device that is moving down on the slope. In this case, the velocity is lowered by controlling the motor that drives wheels prior to turning the brake module operative as set forth above. However, the specific method for motor control at this time is set by assuming as if the device has been moving on the horizontal pathway. Accordingly, the conventional control method may not work well so as to stop the device moving on the slope.

The natural fall force, by which the mobile radiation device is naturally rolling and moving down on the slope, is added the mobile radiation device other than the driving force of the motor that drives wheels and the force by which the operator can push the bar. Accordingly, when the operator operates the brake bar to lower the velocity of the wheeled platform, the rotation of wheels basically must be lowered by the extent of which the natural fall force can be overcome. However, according to the conventional device, no consideration for the fall force has been given. Specifically, even though the operator operates the brake lever, the velocity of the wheeled platform has not been lowered at all and even increases. Such circumstance is deemed dangerous. The brake module becomes operative after the velocity of the wheeled platform is lowered so that it seems that the brake module will never be operable for the wheeled platform moving down on the slope continuously. Accordingly, relative to the device having the conventional structure, the brake module becomes operative after a relatively long time passes from the beginning of the operation of the brake lever so as to ensure the safety. Accordingly, the brake operation to ensure the safety therefor can prevent the wheeled platform from forever move.

However, as the result, it may take a relatively long time to stop the device moving on the slope. In this circumstance, it must be considered that the device may collide against an obstacle in the front of the moving direction.

It seems that if the brake operation is executed at earlier timing to ensure the safety therefor, this kind of the defect can be likely resolved. However, given the control method for the brake operation is set by predicting the move condition on the slope, the device cannot be stopped appropriately while moving on the horizontal pathway this time. Because the device moving on the horizontal pathway is enforced to stop with the control method for the slope, a harsh brake should be given to the device. Then, when the device stops, the device jounces. The operator may feel in many cases that the brake was too strong when the device is stopped on the horizontal pathway or the patient's room. In such circumstance, it must be considered that the operator walking behind the device may collide against the device.

Considering such circumstance, the purpose of the present invention is to provide a mobile radiation device that can be stopped on the horizontal pathway without jounce and can be stopped on the slope pathway in the short period of time.

Means for Solving the Problem

The present invention comprises the following structure to solve the above problem.

Specifically, a mobile radiographic device of the present invention comprises; a wheeled platform, wherein a radiation source that radiates the radiation, a detector that detects the radiated radiation and outputs detected signals are installed thereto, a grip bar that is gripped by the operator while the wheeled platform is moving, a driving means that drives the wheeled platform, a pressure sensor that detects the pressure added to the bar, an assist control means that drives the driving means according to the output from the pressure sensor, a velocity measurement means that measures the move velocity of the wheeled platform, a stop direction input means to input the direction for stopping the wheeled platform from the operator, a brake module that stops the moving wheeled platform, a velocity lowering control means that controls the driving means so as to add the braking force to lower the velocity of the wheeled platform moving on the horizontal pathway prior to turning the brake module operative by inputting the direction from the operator into the stop direction input means, and a brake control means that stops the wheeled platform by turning the brake module operative when the velocity of the wheeled platform is lowered until the predetermined velocity by the velocity lowering control means, wherein (A) the braking control means turns the brake module operative when the velocity of the wheeled platform increases despite beginning of braking the wheeled platform by the velocity lowering control means.

Action and Effect

According to the structure of the present invention, a mobile radiation device that can be stopped on the horizontal pathway without jounce and can be stopped on the slope pathway in the short period of time can be provided. Specifically, a mobile radiographic device of the present invention comprises; a velocity lowering control means that controls the driving means so as to add the braking force to lower the velocity of the wheeled platform moving on the horizontal pathway, and when the velocity of the wheeled platform is lowered until the predetermined velocity, a brake control means that stops the wheeled platform by turning the brake module operative. According to this structure, the wheeled platform moving on the horizontal pathway will not be given the harsh brake and even when the move is stopped, the device will not jounce.

Further, the present invention provides the idea in the case of moving on the slope pathway. Specifically, the braking control means turns the brake module operative when the velocity of the wheeled platform increases despite beginning of braking the wheeled platform by the velocity lowering control means. In some cases, when the wheeled platform is stopped while moving on the slope, the control by the velocity lowering control means may not lower the velocity of the wheeled platform and rather increases the velocity. In such cases, according to the present invention, when the velocity of the wheeled platform increases despite beginning of braking the wheeled platform by the velocity lowering control means, the brake module can be turned operative promptly so that the incident in which the wheeled platform continues to move for a long time ignoring the direction of stop to the wheeled platform moving on the slope can be controlled.

Further, a mobile radiographic device of the present invention comprises; a wheeled platform, wherein a radiation source that radiates the radiation, a detector that detects the radiated radiation and outputs detected signals are installed thereto, a grip bar that is gripped by the operator while the wheeled platform is moving, a driving means that drives the wheeled platform, the pressure sensor that detects the pressure added to the bar, the assist control means that drives the driving means according to the output from the pressure sensor, a velocity measurement means that measures the move velocity of the wheeled platform, a stop direction input means to input the direction for stopping the wheeled platform from the operator, a brake module that stops the moving wheeled platform, a velocity lowering control means that controls the driving means so as to add the braking force to lower the velocity of the wheeled platform moving on the horizontal pathway prior to turning the brake module operative by inputting the direction from the operator into the stop direction input means, and the brake control means that stops the wheeled platform by turning the brake module operative when the velocity of the wheeled platform is lowered until the predetermined velocity by the velocity lowering control means, and (B1) a memory means that stores the time-course of the velocity obtained by the actual measurement of the velocity in advance when the velocity of the wheeled platform moving on the horizontal pathway is lowered by the velocity lowering control means, and (B2) the velocity lowering control means is operative to strengthen the braking force of said driving means when it is found that the state is the short velocity decrease state, wherein the velocity decrease of said wheeled platform after beginning of braking said wheeled platform is less than the decrease expected from said time-course.

Action and Effect

The inventor set forth that the structure of the present invention can provide another Embodiment to solve the problem of the present invention. Specifically, according to the structure of the present invention, a mobile radiation device that can be assuredly stopped on the horizontal pathway without jounce and can be stopped on the slope pathway in the short period of time can be provided. The rationale that the device can be stopped without jounce on the horizontal pathway is based on the same structure as previously described.

Further, the present invention provides the idea in the case of moving on the slope pathway. This mode is different from the previous structure. Specifically, the velocity lowering control means is operative to increase the braking force of the driving means when the velocity decrease of the wheeled platform after beginning of braking the wheeled platform is out of the time-course indicating the ideal change of the velocity of the wheeled platform. In some case, when the wheeled platform moving on the slope is being stopped, the velocity decrease of the wheeled platform may not be satisfactory because of the shortage of the braking force of the driving means. In such cases, according to the present invention, despite beginning of braking the wheeled platform by the velocity lowering control means, when the velocity of the wheeled platform increases, the brake module can be turned operative promptly so that the incident in which the wheeled platform continues to move for a long time ignoring the direction of stop to the wheeled platform moving on the slope can be controlled.

Further, the mobile radiation device of the present invention may comprise both (A) and (B1), (B2).

Further, it is more preferable that relative to the above mobile radiation device having (B1), (B2), the velocity lowering control means searches the initial velocity as the velocity of the wheeled platform at the beginning point of the operation of the velocity lowering control means from the time-course, recognizes the velocity level of the initial velocity relative to the time-course after a predetermined time is past, and when the actual velocity of the wheeled platform after the predetermined time from the initial point of the operation is higher than the recognized velocity, it is decided that the wheeled platform is in the short velocity decrease state.

Action and Effect

The above structure illustrates further specific mode of the mobile radiation device of the present invention. Given the velocity lowering control means decides whether the velocity decrease of the wheeled platform is unsatisfied or not based on the time-course indicating ideal velocity decrease of the wheeled platform, the velocity lowering control means assuredly can recognize the unsatisfied velocity decrease of the wheeled platform and can be operative.

Further, it is more preferable that the above mobile radiation device is for a round.

Action and Effect

The present invention is applicable to a mobile radiation device for rounding.

Effects of the Invention

According to the structure of the present invention, the structure is improved as the mobile radiation device can be assuredly stopped on the horizontal pathway without jounce. Specifically, the present invention provides the idea in the case of moving on the slope pathway. The braking control means of the present invention turns the brake module operative when the velocity of the wheeled platform increases despite beginning of braking the wheeled platform by the velocity lowering control means. According to the present invention, when the velocity of the wheeled platform increases despite beginning of braking the wheeled platform by the velocity lowering control means, the brake module can be turned operative promptly so that the incident in which the wheeled platform continues to move for a long time ignoring the direction of stop to the wheeled platform moving on the slope can be controlled.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
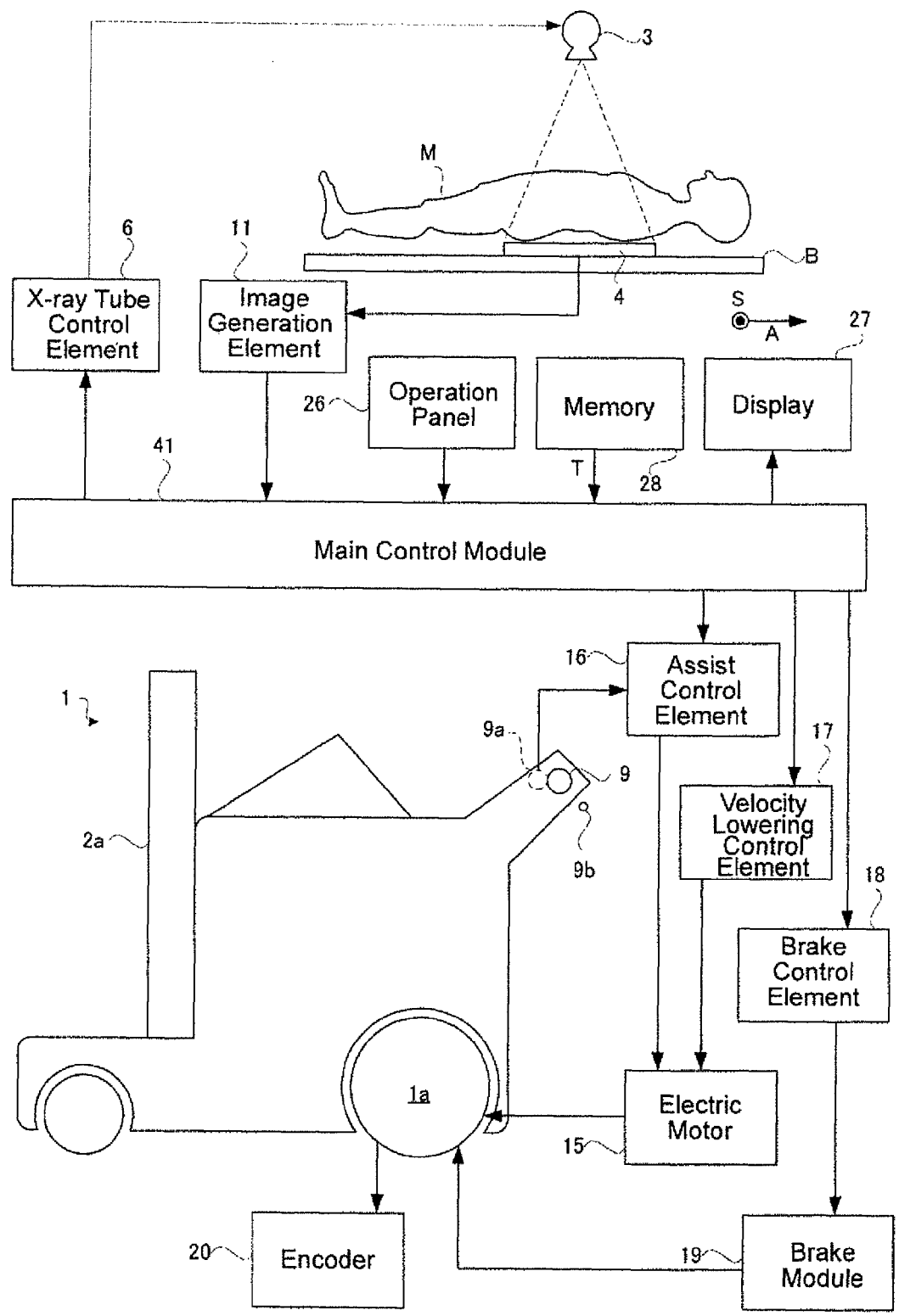
FIG. 1 is a functional block diagram illustrating the total structure of the mobile X-ray imaging device of Embodiment 1.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

The Best Mode of Embodiment of the Present Invention

A mobile radiographic device of the present invention is an imaging device for rounding. Hereafter, the inventor illustrates the best mode of each Embodiment of the present invention. Further, an X-ray of Embodiment corresponds to the radiation of the present invention.

Embodiment 1

Figure 2:
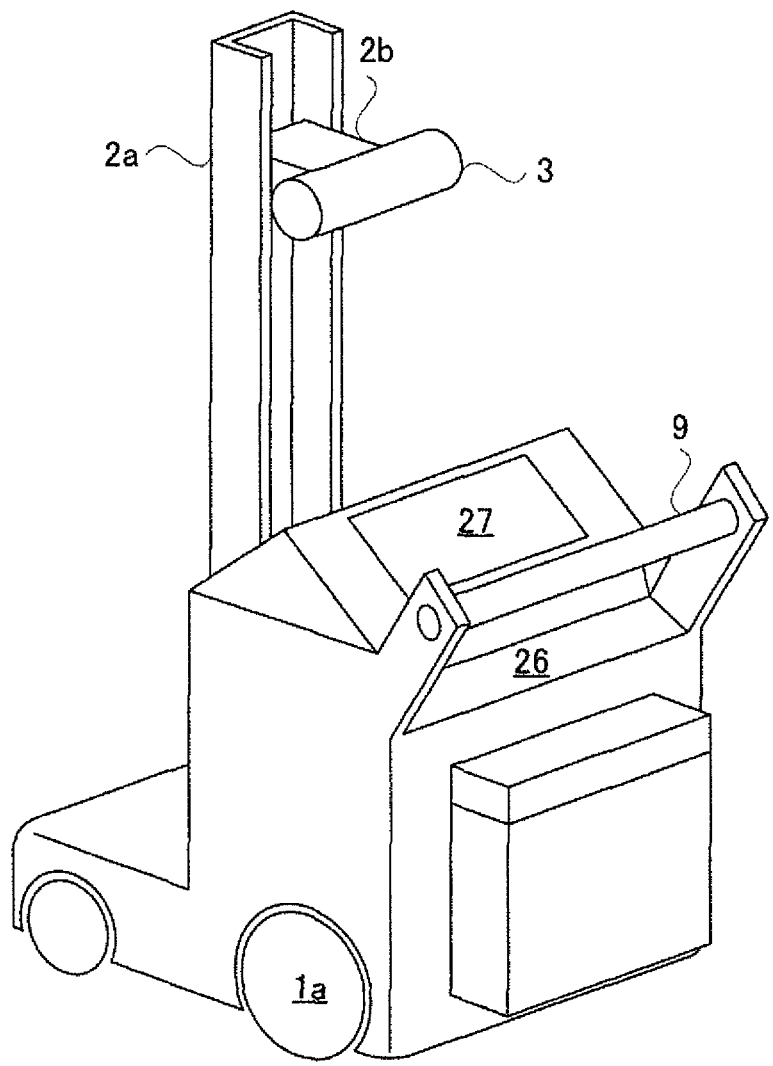
FIG. 2 is a perspective view illustrating the total structure of the mobile X-ray imaging device of Embodiment 1.
Figure 3:
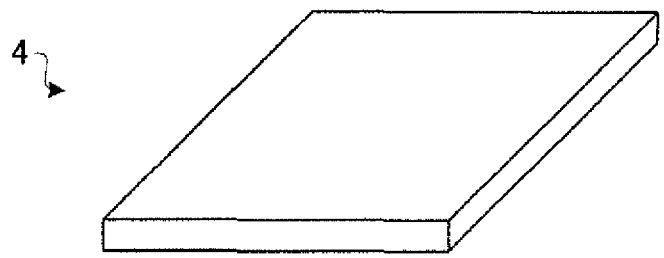
FIG. 3 is a perspective view illustrating the FPD of Embodiment 1.
Figure 4:
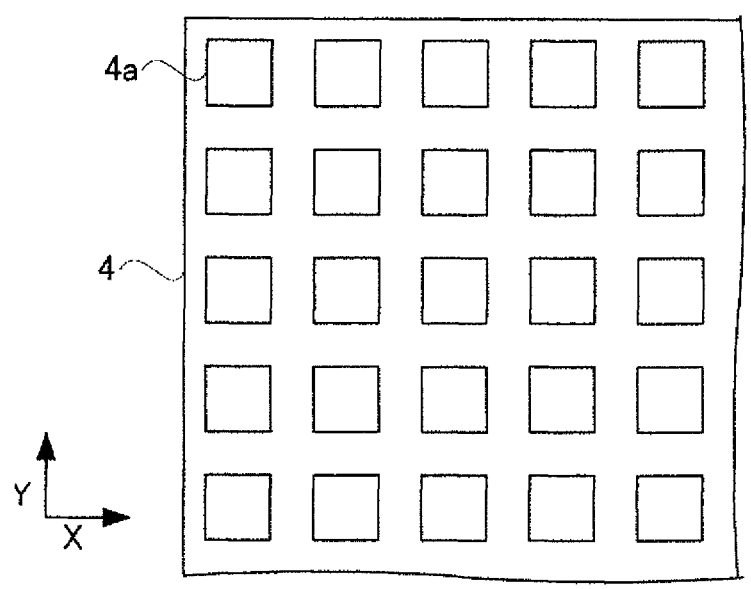
FIG. 4 is a plan view illustrating the FPD of Embodiment 1.

Hereinafter, the inventor sets forth the mobile radiation device of Embodiment. FIG. 1 is a block diagram illustrating the structure of the control system of the mobile X-ray imaging device of Embodiment of the present invention. FIG. 2 is a perspective view illustrating the aspect of the device of Embodiment. FIG. 3 is a perspective view illustrating the flat panel type X-ray detector (X-ray image receiving module) installed to the device of Embodiment. FIG. 4 is a plan view illustrating the array state of the X-ray detection elements of the flat panel type X-ray detector of the device of Embodiment. An X-ray is one example of radiations of the present invention and FPD stands for Flat Panel Detector.

Referring to FIG. 1 and FIG. 2, relative to the mobile radiation device of Embodiment, a set of required modules including an X-ray tube 3 that irradiates X-ray to the subject M as the imaging target, a flat panel type X-ray detector (hereafter FPD) 4 that detects the irradiated X-ray from the X-ray tube 3 and acquire a transmissive X-ray image of the subject M and an X-ray tube control element 6 that controls the X-ray tube 3, and so forth, are installed to the wheeled platform having four wheels and a rear wheel driving structure. Accordingly, the device of Embodiment along with move of the wheeled platform can structurally move toward the patient's room where the imaging target M is laying. The X-ray tube 3 that radiates the radiation and the FPD 4 that detects the radiated radiation and outputs detected signals are mounted to the wheeled platform, The X-ray tube 3 corresponds to the radiation source of the present invention.

That is, the device of Embodiment is capable of performing X-ray imaging in the patient room so that the subject M may not be required to go a roentgen room, and is so-called a device type capable of round imaging.

Referring to FIG. 2, the X-ray tube 3 is mounted in the tip of the support arm 2b that is installed to the support column 2a standing perpendicular in the front side of the wheeled platform in the horizontal state and is operative so as to move up-and-down. The support column 2a is revolvable around the center axis as the revolving axis while keeping the standing state and when the wheeled platform 1 is moving, the support column 2b with the X-ray tube 3 is set in-place in the rear side of the support column 2a by which the X-ray tube may not disturb the move. And when imaging, the support column 2a is revolved to set the support arm 2b with the X-ray tube 3 in-place in the front side of the support column 2a and further according to necessity, the support arm 2b is moved up-and-down along the support 2a so that the height of the X-ray tube 3 can be adjusted appropriately.

Referring to FIG. 3, the FPD 4 is a plate like device to which a wireless communication module so as to output the detection signals to the main body of the wheeled platform and input the control signal from the main body of the wheeled platform. The FPD 4 detects the radiated X-ray and outputs the detection signal. The FPD 4 is usually stored inside the wheeled platform 1 and taken out prior to imaging and set underside of the subject M. At this time, the FPD 4 and the wheeled platform 1 are interactively operative to send and receive the data via the wireless communication module. Accordingly, the wheeled platform 1 per se is equipped with the wireless communication module. The communication modules installed to the FPD 4 and the wheeled platform send and receive the data so that the FPD 4 can acquire the information as to a control from the wheeled platform 1 when imaging. In addition, the wheeled platform 1 can acquire the detection signal sent from the FPD 4. The FPD 4 corresponds to the detection means of the present invention.

The inventor sets forth the structure of the FPD 4. Referring to FIG. 4, the FPD 4 structurally is a two dimensional X-ray detector in which a number of X-ray detection elements 4a are arrayed lengthwise and breadthwise (X, Y directions) on the X-ray detection surface receiving X-ray, and detects by converting the projected transmissive X-ray image on the X-ray detection surface to the electric signal as the detection signal for X-ray image acquisition with the X-ray detection element 4a. The FPD 4 is a direct-conversion type X-ray imaging device and constitutes a variety of laminated layers including an amorphous layer and so forth.

A storage holder to store the FPD 4 is installed to the wheeled platform 1. Referring to FIG. 1, the FPD 4 taken out from the storage holder is set in the imaging place under the subject M lying on the bed B.

The inventor sets forth the display 27. The display 27 that displays the necessary information/data for X-ray imaging and the operation panel 26 that is operative to conduct the necessary operation for X-ray imaging and move of the wheeled platform are installed to the upper side of the wheeled platform 1 (referring to FIG. 2), and structurally an operation menus and X-ray image and so forth are displayed on the display 27 in accordance with the operation contents of the operation panel 26 and progression of X-ray imaging.

The inventor sets forth the X-ray control element 6. The X-ray tube control element 6 that controls the necessary control for the X-ray imaging allows the X-ray tube 3 to radiate X-ray exactly following the X-ray imaging conditions including the predetermined electric voltage, tube current and so forth for performing X-ray imaging. Further, the mobile radiation device relative to Embodiment 1 comprises the image generation element 11 to acquire the X-ray image corresponding to the transmissive X-ray image of the subject M based on the detection signals output from the FPD 4.

Further, according to the device of Embodiment 1, the wheeled platform 1 can be structure-wise electrically movable. Specifically, the wheeled platform 1 moves when the rear wheels is of the wheeled platform 1 rotate along with that the assist control element 16 rotates the electric motor 15 following the driving operation conducted by the operator through the panel 26. Further, the electric motor 15 is not mandatory for the front wheel of the wheeled platform 1.

The electric motor 15 that structure-wise drives the wheeled platform 1 corresponds to the driving means of the present invention, The bar 9 that is gripped by the operator is installed to the wheeled platform 1. The bar 9 that is gripped by the operator while the wheeled platform 1 is moving. When the operator pushes the bar 9, the sensor 9a installed to the bar 9 senses the pressure and detects the strength and direction of the pressure on the bar 9. The pressure sensor 9a outputs the data as to the pressure of the bar 9 to the assist control element 16. The assist element 16 controls the rear wheels 1a so as to move the wheeled platform 1 in the direction to which the bar 9 is pushed. The assist control element 16 drives the electric motor according to the power output from the pressure sensor 9a. The assist control element 16 corresponds to the assist control means of the present invention.

Figure 5:
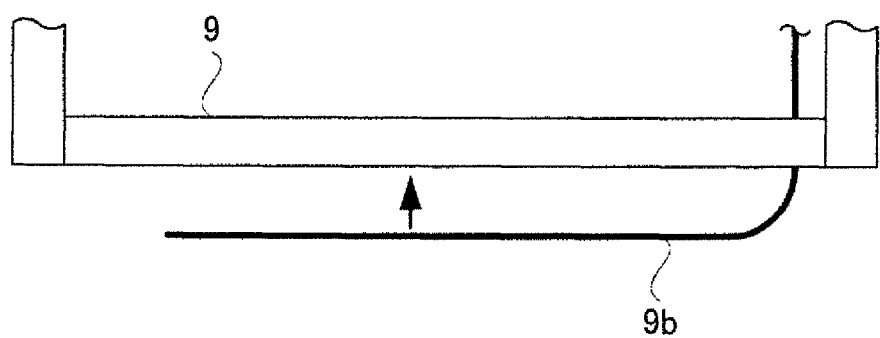
FIG. 5 is a schematic diagram illustrating a brake lever of Embodiment 1.

A brake lever 9b that is operative to stop the wheeled platform 1 by the operator is installed to the bar 9, Referring to FIG. 5, the brake lever 9b is like a rod extending in the same direction as the bar 9 extends. The brake lever 9b is movable relative to the bar 9 and the operator can move the brake lever 9b closer to the bar 9 while keeping parallel state to the bar 9. When the operator wants to move the wheeled platform 1, the operator moves the brake lever 9b closer to the bar 9. Then, the lock due to the brake module 19 is released and the wheeled platform 1 can be movable. The release of the lock of the wheeled platform 1 can be kept while the operator is keeping the brake lever 9b closer to the bar 9. Then, when the operator unlinks hands from the brake level 9b while the wheeled platform is moving, the brake lever 9b automatically leaves the bar 9. At this time, as if the operator inputs the direction to stop the wheeled platform 1, the wheeled platform 1 will stop. The brake lever 9b is to input the direction for stopping the wheeled platform 1 from the operator and corresponds to the stop direction input means of the present invention.

The brake module 19 is an electromagnetic brake that can bring the stop of the moving wheeled platform 1 in reality. The brake module 19 is a drum type and may stop the rotation of the wheel axis of the rear wheels 1a by using e.g., a brake shoe. The purpose of the brake module 19 is to lower the velocity of the wheeled platform 1 and stop the wheeled platform 1 at the end. The brake control element 18 controls the brake module 19. The brake control element 18 has the structure to turn the brake module 19 operative when the operator directs to stop the wheeled platform through the brake lever 9b. The brake control element 18 corresponds to the brake control means of the present invention.

Given the brake module 19 is turned to be operative immediately after the operator operates the brake lever 9b, a harsh braking for the wheeled platform. 1 takes place. The harsh braking should be prevented because of not only providing a strong vibration to the wheeled platform 1 but also the operator walking behind the wheeled platform 1 collides against the wheeled platform 1. Relative to the structure of Embodiment 1, the velocity lowering control element 17 is installed on purpose to prevent the harsh brake of the wheeled platform 1. The velocity lowering control element 17 that controls the electric motor 15 so as to add the braking force to lower the velocity of the wheeled platform 1 moving on the horizontal pathway prior to turning the brake module 19 operative by that the operator inputs the direction to the brake lever 9b. It should be paid attention that the velocity lowering control element 17 does not control the brake module 19 but controls the electric motor 15. The velocity lowering control element 17 corresponds to the velocity lowering control means of the present invention.

Figure 6:
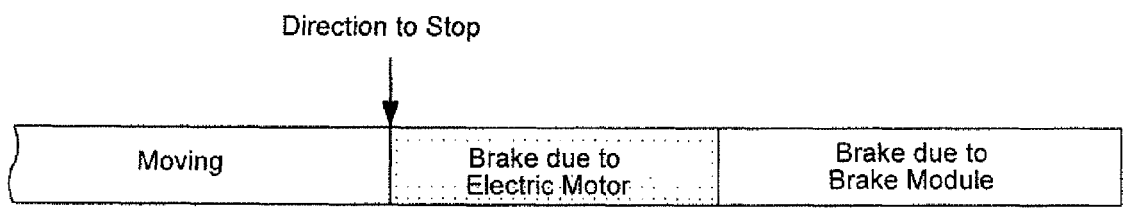
FIG. 6 is a timing chart illustrating a brake operation of Embodiment 1.

FIG. 6 is illustrating the braking mode for the wheeled platform 1 when the operator directs to stop the wheeled platform 1 through the brake lever 9b. When the moving wheeled platform 1 is directed to stop, first instead of the assist control element 16, the velocity lowering control element 17 controls the electric motor 15. At this point, the brake module 19 is not operative. When the velocity lowering control element 17 continuously controls the electric motor 15 for a certain period of time, the velocity of the wheeled platform 1 may decrease to the level at which the wheeled platform 1 may not greatly jounce despite turning the brake module 19 operative. The brake module 19 becomes operative at this point and the wheeled platform 1 is assuredly stopped. Accordingly, braking of the wheeled platform 1 when the wheeled platform 1 of Embodiment 1 is stopped is conducted by two steps including controlling the electric motor 15 and turning the brake module 19 operative.

Figure 7:
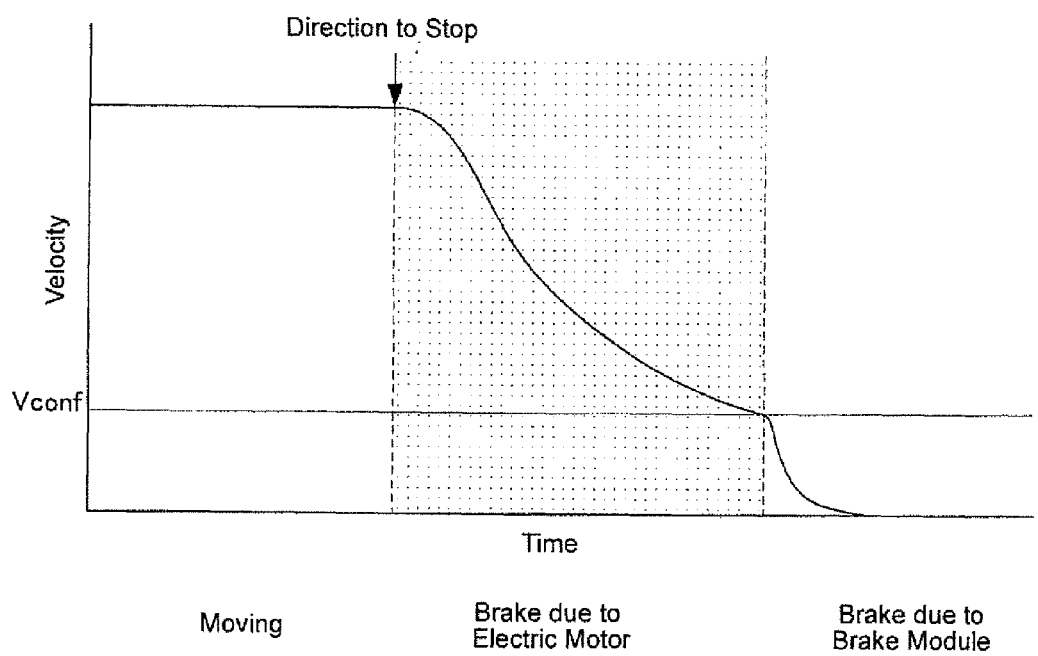
FIG. 7 is a time-course illustrating a brake operation of Embodiment 1.

FIG. 7 is illustrating the relationship between the velocity of the wheeled platform 1 and the time when braking is conducted by following two steps described above. For simplicity, the velocity of the moving wheeled platform 1 is given as constant. When the direction for stop is given by the operator through the brake lever 9b, the direction is sent to the velocity lowering control element 17. Then, the velocity lowering control element 17 controls the electric motor 15 so as to rotate the wheel axis of the rear wheels 1a toward opposite direction to the rotation direction of the rotating rear wheel 1a. Then the rear wheels 1a will not actually rotates reversely and instead, the rotation of the rear wheel gradually becomes slow. Accordingly, the velocity of the wheeled platform 1 gradually decreases. The braking due to the electric motor 15 is relatively weak.

The velocity of the wheeled platform 1 continuously and smoothly decreases due to braking of the electric motor 15 and when the velocity reaches to the predetermined value Vconf, the brake control element 18 turns the brake module 19 operative. When the brake control element 18 turns the brake module 19 operative, the velocity of the wheeled platform decreases until the predetermined velocity with control of the velocity lowering control element 17. Then, the strong brake as if locking the rear wheels 1a is given so that the wheeled platform 1 can be quickly and assuredly stopped. When the brake module 19 is turned operative, the velocity of the wheeled platform 1 has decreased sufficiently so that a harsh brake may not be given to the wheeled platform 1 despite turning the brake module 19 operative. Accordingly, the wheeled platform 1 of Embodiment 1 may stop without jounce. Further, after the action of the brake control element 18 starts, the velocity lowering control element 17 do not always have to continuously control the electric motor 15.

Meantime, when the brake control element 18 is operative, the referred velocity of the wheeled platform 1 is being measured by an encoder 20 installed to the wheel axis of the rear wheels 1a. The encoder 20 is a sensor measure the rotation velocity of the wheel axis. The output from the encoder 20 is sent to the brake module 19 from time to time. The encoder 20 is structure-wise operative to measure the moving velocity of the wheeled platform 1 and corresponds to the velocity measurement means of the present invention.

Figure 8:
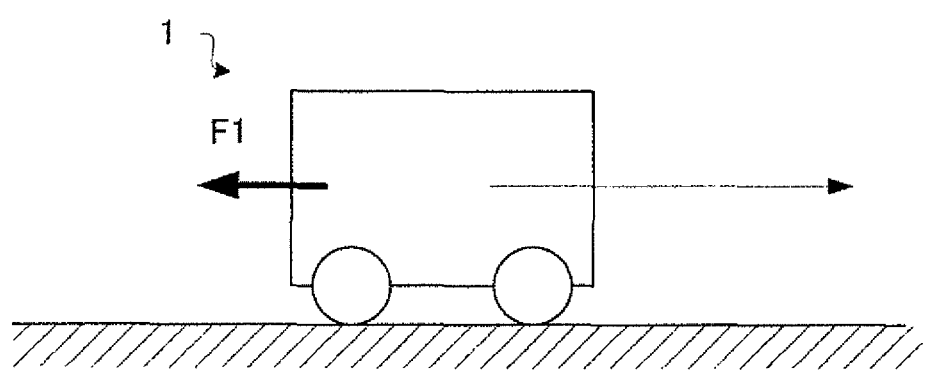
FIG. 8 is a schematic diagram illustrating a brake operation of Embodiment 1.

The inventor sets forth the control method of the electric motor 15 that is conducted by the velocity lowering control element 17. Referring to FIG. 8, the level of braking strength so as to reversely rotate the electric motor 15 is controlled for the velocity lowering control element 17 to brake the rear wheels 1a is set given the wheeled platform is moving on the horizontal pathway. Referring to FIG. 8, the wheeled platform 1 is moving from the left side to the right side. Accordingly, as indicated as F1 in FIG. 8, the electric motor 15 should be controlled so as to reversely rotate in order to move the wheeled platform 1 in the opposite direction against the traveling direction of the wheeled platform 1 to brake the wheeled platform 1 in such mode. The strength of reverse rotation thereof is the level at which the force to control the inertial motion of the wheeled platform 1 as indicated as the fine arrow in FIG. 8, and the rotation axis of the electric motor 15 will not be in the reversed rotation direction actually and the rotation of the rotation axis gradually slows down. The data that illustrates the strength of the reverse rotation that the velocity lowering control element 17 refers in the control mode can be acquired by selecting the best mode by decreasing the velocity by different strength of the reverse rotation as to the moving wheeled platform 1 in the actual mode or by performing the simulation.

[Characteristic Components of the Present Invention]

Figure 9:
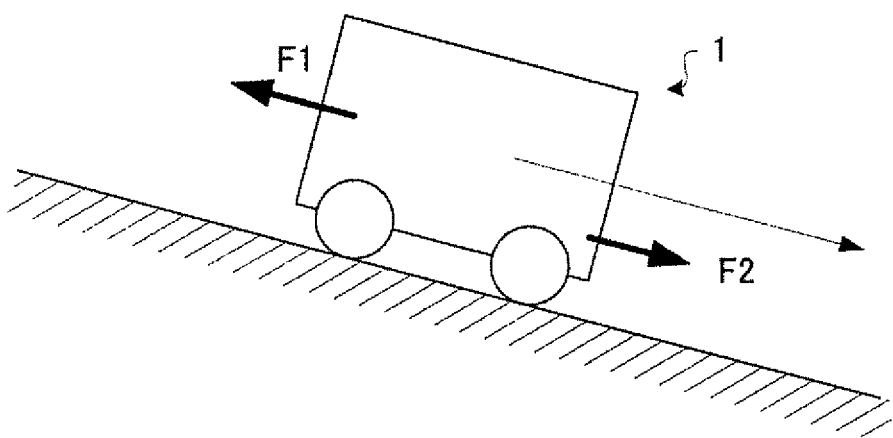
FIG. 9 is a schematic diagram illustrating a brake operation of Embodiment 1.

The wheeled platform 1 based on only the above components cannot correspond when moving on the slope. Because the precondition of the control of the velocity lowering control element 17 is that the wheeled platform 1 is passing on the horizontal pathway. The inventor specifically sets forth the mode thereof. FIG. 9 is illustrating that the wheeled platform 1 is moving on the down slope pathway. Even if the velocity lowering control element 17 controls the electric motor 15 to stop the wheeled platform 1, as set forth referring to FIG. 8, the only force F1 that can only control the inertial motion of the wheeled platform 1 indicated by the fine arrow in FIG. 8 can be added to the wheeled platform 1. Referring to FIG. 9, the force F2 takes place when the wheeled platform 1 rolls down due to gravity, other than the inertial motion of the wheeled platform 1. The velocity lowering control element 17 is not counting the force F2 that takes place when the wheeled platform 1 is moving on the slope so that the incident in that the wheeled platform 1 moves forever without decreasing the velocity because of only decreasing the velocity by the velocity lowering control element 17 thereof can take place.

Figure 10:
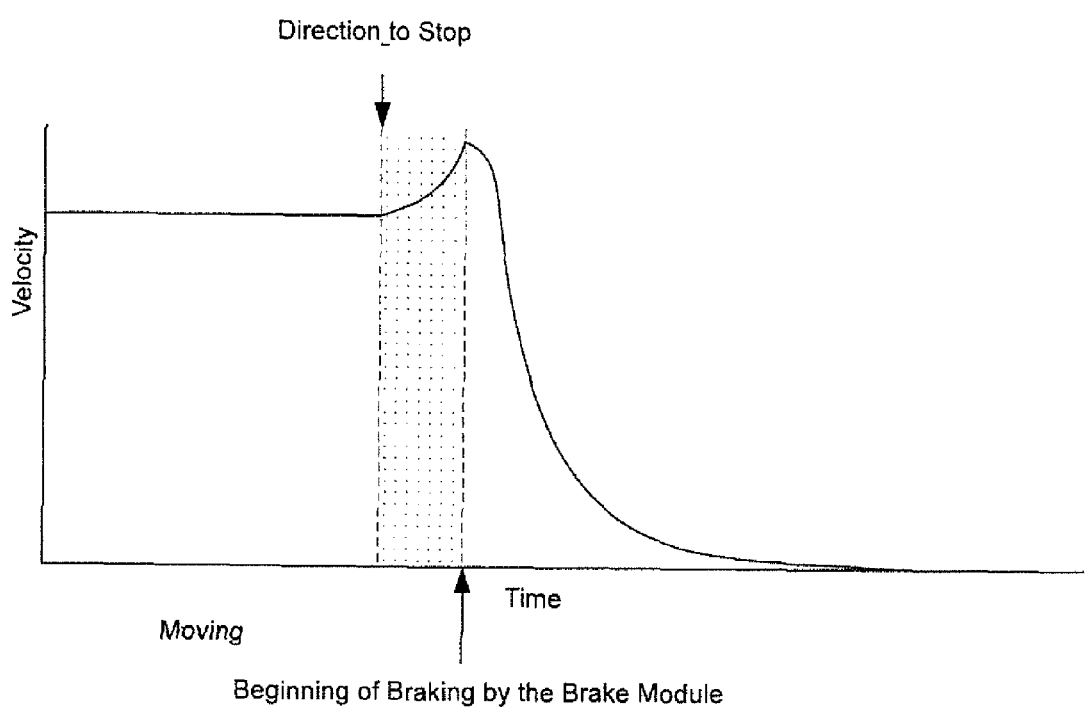
FIG. 10 is a time-course illustrating a brake operation of Embodiment 1.

Then, the structure of Embodiment adopts the following structure as the wheeled platform 1 moving on the slope can assuredly stop. Specifically, referring to FIG. 10, the brake control element 18 turns the brake module 19 operative immediately before the velocity of the wheeled platform 1 is lower than the setup value Vconf when the wheeled platform 1 is accelerated from the beginning point of braking of the wheeled platform 1 by the velocity lowering control element 17. Specifically, the braking control element 18 turns the brake module 19 operative when the velocity of the wheeled platform increases despite beginning of braking the wheeled platform 1 by the velocity lowering control element 17.

The brake module 19 is controlled in such mode so that the brake distance that is the distance that the wheeled platform 1 travels between the stop direction given to the wheeled platform 1 moving on the slope by the operator through brake bar 9b and the actual stop of the wheeled platform 1 can be shorten. At this time, even though no guarantee relative to the harsh brake is given, the immediate and powerful braking independently from the brake of the electric motor 15 is required under the state in that the force F2 that accelerates naturally the wheeled platform 1 is given to the wheeled platform 1. Accordingly, it is more preferable that a strong braking independent from the electric motor 15 to assuredly stop the wheeled platform 1 moving on the slope is provided.

[Operation of Each Element after the Brake Lever is Turned Operative]

Figure 11:
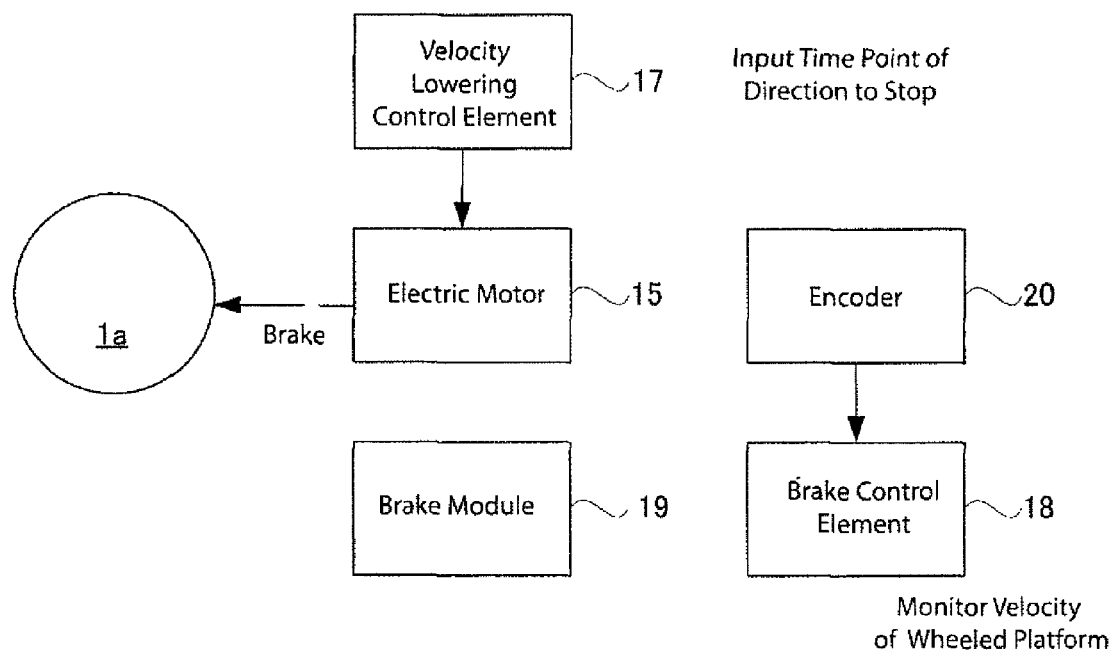
FIG. 11 is a functional schematic diagram illustrating a brake operation of Embodiment 1.

The inventor sets forth the operation of each element 15, 17, 18, 19, 20 when the above wheeled platform 1 is going to be stopped. Referring to FIG. 11, the aspect of each element is illustrated when the direction to stop the wheeled platform 1 is given by the operator. At this point, the velocity lowering control element 17 controls the electric motor 15 so as to reversely rotate and brakes the rear wheels 1a. On the other hand, the encoder 20 sends out the data relative to the velocity of the wheeled platform 1 to the brake control element 18 from time to time. The brake control element 18 is monitoring the velocity of the wheeled platform 1 through the encoder 20 from time to time.

Figure 12:
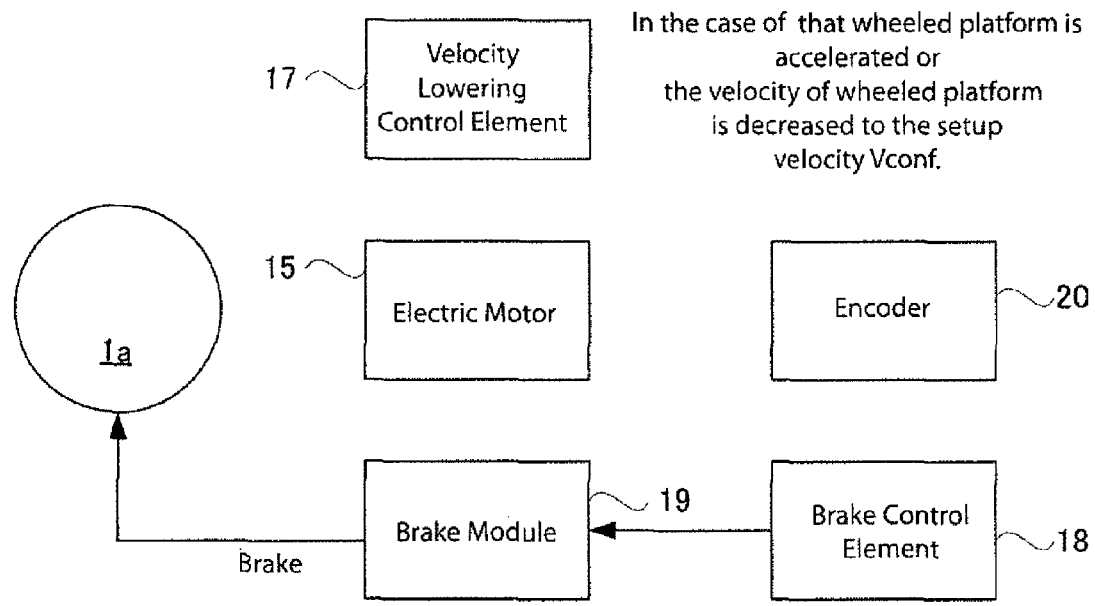
FIG. 12 is a functional schematic diagram illustrating a brake operation of Embodiment 1.

On the other hand, referring to FIG. 12, the operation of each element is illustrated when the wheeled platform 1 accelerates despite the direction to stop the wheeled platform 1 from the operator. At this point, the brake control element 18 turns the brake module 19 operative so that the rear wheels 1a can be braked by the brake module 19. Further, also when the velocity of the wheeled platform 1 decreases steadily without accelerating from the state in FIG. 11 following the direction to stop the wheeled platform 1 from the operator and then even when the velocity of the wheeled platform 1 reaches to the Vconf, the operation of each element can be the same as illustrated in FIG. 12.

[Other Structures of the Mobile Radiation Device of Embodiment]

The main control element 41 is installed to comprehensively control each control element. The main control element 41 comprises a CPU and brings each element 6, 11, 16, 17, 18 into reality by executing a variety of programs, or the above each element can be divided to the calculation module in charge of each element and then executed. The memory 28 stores the setup values of e.g., Vconf and all of a variety of parameters as to the control methods that the velocity lowering control element 17 refers. The memory 28 corresponds to the memory means of the present invention.

As set forth above, according to the structure of the present invention, an mobile radiation device that can be assuredly stopped on the horizontal pathway without jounce and can be stopped on the slope pathway in the short period of time can be provided. Specifically, the mobile radiation device of the present invention comprises the velocity lowering control element 17 that controls the electric motor 15 so as to add the braking force to the wheeled platform 1 to decrease the velocity of the wheeled platform 1 moving on the horizontal pathway, and the brake control element 18 that turns the brake module 19 operative to stop the wheeled platform 1 when the velocity of the wheeled platform 1 decreases to the predetermined velocity. According to this structure, the harsh brake will not be given to the wheeled platform 1 moving on the horizontal pathway, and even when the move is stopped, the device will not jounce.

Further, the present invention provides the idea in the case of moving on the slope pathway. Specifically, the braking control element 18 turns the brake module 19 operative when the velocity of the wheeled platform 1 increases despite beginning of braking the wheeled platform 1 by the velocity lowering control element 17. In some cases, when the wheeled platform 1 is stopped while moving on the slope, the control of the electric motor 15 by the velocity lowering control element 17 may not lower the velocity of the wheeled platform 1 and rather increases the velocity. In such cases, according to the present invention, despite beginning of braking the wheeled platform 1 by the velocity lowering control element 17, when the velocity of the wheeled platform 1 increases, the brake module 19 can be turned operative promptly so that the condition in which the wheeled platform 1 continues to move for a long time ignoring the direction of stop to the wheeled platform 1 moving on the slope can be controlled.

Embodiment 2

Next, the inventor sets forth the structure of the mobile radiation device of Embodiment 2. The structure of the mobile radiation device of Embodiment 2 is almost the same as the device set forth in Embodiment 1. Accordingly, an explanation of the common element of the structure of Embodiment 2 to Embodiment 1 here is skipped. Specifically, the device of Embodiment 2 is structure-wise operative to stop the wheeled platform 1 by two steps braking as set forth above when the operator directs to stop the wheeled platform through the brake lever 9b.

Figure 13:
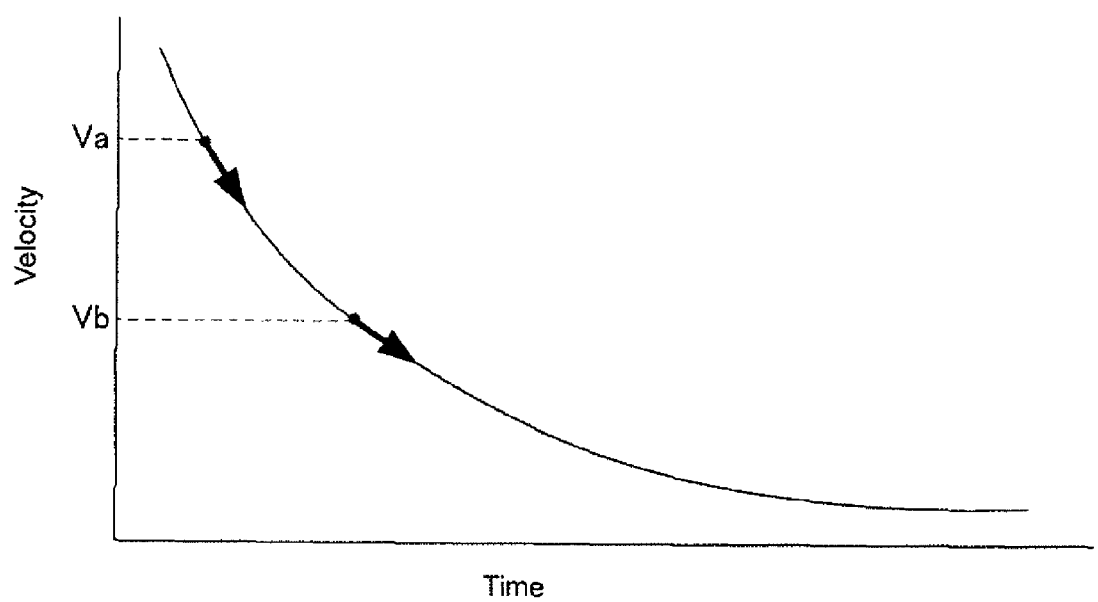
FIG. 13 is a graph illustrating the data related to Embodiment 2.

The different point of the device of Embodiment 2 from Embodiment 1 is the control method of the velocity lowering control element 17. Hereafter, the inventor specifically set forth the control method. FIG. 13 illustrates the related data indicating the relationship between the velocity and the time stored in the memory 28. The related data is the time-course that indicates how the velocity of the wheeled platform 1 changes when the velocity lowering control element 17 brakes the wheeled platform 1 through the electric motor 15.

The time-course can be obtained by measuring the velocity change of the wheeled platform 1 with the encoder 20 while adding brake to the wheeled platform 1 moving on the horizontal pathway by the electric motor 15. Specifically, the time-course represents so-to-speak the ideal velocity change that represents how the velocity of the wheeled platform 1 changes when the wheeled platform 1 moving on the horizontal pathway is braked by the electric motor 15. Relative to the case of that the wheeled platform 1 actually stops, the case of that the velocity change is not as-is the time-course (as ideal) is considered e.g., the case of that the wheeled platform 1 is moving on the slope pathway. The memory 28 stores the time-course of the velocity obtained by the actual measurement of the velocity in advance when the velocity of the wheeled platform 1 moving on the horizontal pathway is lowered by the velocity lowering control element 17.

Meantime, the velocity of the wheeled platform 1 changes depending on the pressure level of the bar 9 by the operator who tries to move the wheeled platform 1. Accordingly, the velocity of the wheeled platform 1 cannot be obtained right before until the operator directs to stop the wheeled platform and therefore must not be predicted in advance. It is suspected that the aspect of the velocity decrease of the wheeled platform 1 can be expressed only by the time-course in that the velocity and the time are simply related as illustrated in FIG. 13 even though the velocity of the wheeled platform 1 being stopped should be different every stop-operation. Conclusively speaking as to this problem, the velocity change of the wheeled platform 1 after beginning of braking by the electric motor 15 can be assuredly represented, independently from the velocity of the moving wheeled platform 1, by the time-course illustrated in FIG. 13.

The inventor sets forth the rationale therefor. For example, the case in that the operator moves the wheeled platform 1 in a hurry is considered. At this time, the velocity of wheeled platform 1 is Va. Then, the braking of the wheeled platform 1 by the electric motor 15 begins from the state in which the velocity of the wheeled platform 1 is Va. The state of the wheeled platform 1 immediately after the beginning of braking corresponds to the position of Va on the time-course in FIG. 13. From this point, the velocity of the wheeled platform 1 decreases by the braking due to the electric motor 15 according to the time change. The aspect of the velocity decrease copies the time-course in fact. Specifically, the braked velocity of the wheeled platform 1 decreases along with the time-course graph of FIG. 13 as the beginning at the position corresponding to Va on the time-course indicated by the arrow in FIG. 13.

For example, the case in that the operator moves the wheeled platform 1 slowly is considered. At this time, the velocity of wheeled platform 1 is Vb. Then, the braking of the wheeled platform 1 by the electric motor 15 begins from the state in which the velocity of the wheeled platform 1 is Vb. The state of the wheeled platform 1 immediately after the beginning of braking corresponds to the position of Vb on the time-course in FIG. 13. From this point, the velocity of the wheeled platform 1 decreases by braking of the electric motor 15 according to the time change. The aspect of the velocity decrease copies the time-course as well. Specifically, the braked velocity of the wheeled platform 1 decreases along with the time-course graph of FIG. 13 as the beginning at the position corresponding to Vb on the time-course indicated by the arrow in FIG. 13. Specifically, the time of the abscissa in FIG. 13 is relative and the position corresponding to the beginning of braking will change according to the velocity of the wheeled platform 1.

Accordingly, if the time-course is applied, the velocity change of the wheeled platform 1 after braking can be predicted from the velocity of the wheeled platform 1 before braking. However, the certain time-course is taking care of the issue of the braking due to the electric motor 15 and it is necessary to pay attention that the braking due to the brake module 19 is out of consideration. Accordingly, the velocity prediction is effective from the beginning of braking due to the velocity lowering control element 17 until the time when the brake module 19 is turned operative. The time-course per se is the data that is referred by the velocity lowering control element 17 so that no problem as to the operation of the device takes place even though the time-course is not considering the brake module 19.

[Operation of Velocity Lowering Control Element]

The velocity lowering control element 17 of Embodiment 2 is operative using the time-course illustrated in FIG. 13 in the different mode from Embodiment 1. Specifically, the velocity lowering control element 17 of Embodiment 2 is structure-wise operative to change the control of the electric motor 15 when it is decided that the actual velocity change of the wheeled platform 1 is different from the ideal change by recognizing the change of ideal velocity of the wheeled platform 1 based on the time-course.

Figure 14:
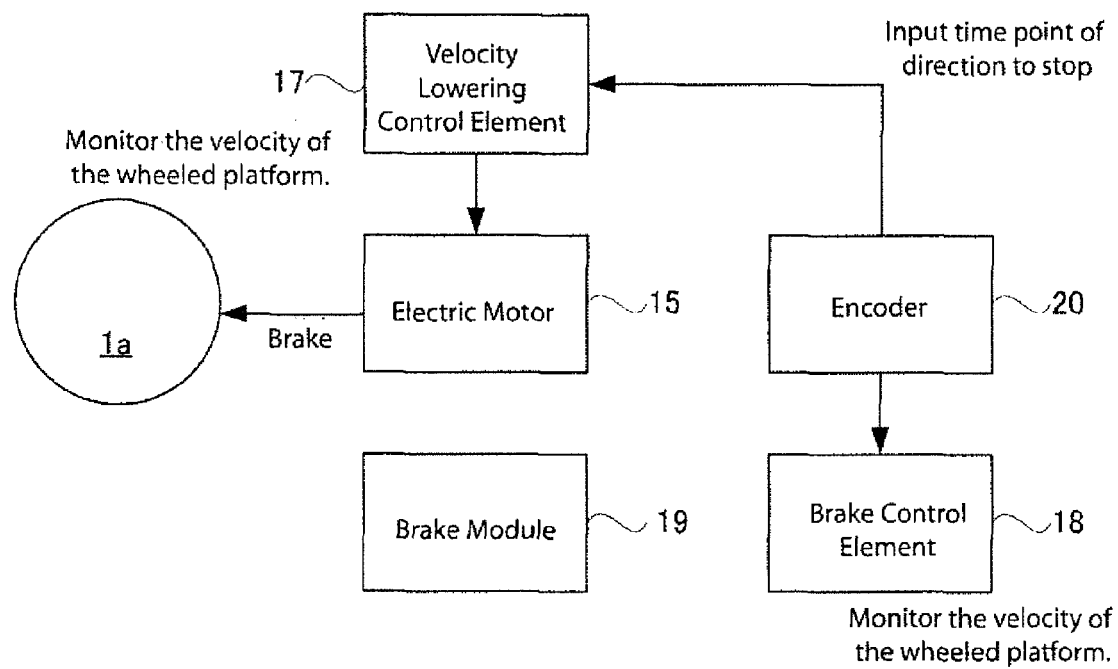
FIG. 14 is a functional schematic diagram illustrating a brake operation of Embodiment 2.

The inventor specifically sets forth the aspect in that the velocity lowering control element 17 decreases the velocity of the wheeled platform 1. The operator directs to stop the wheeled platform 1 moving with the initial velocity V0 through the brake lever 9b. The time when the direction for stop is given is T0. FIG. 14 is illustrating the relationship of each element when the velocity of the wheeled platform 1 is being decreased by the velocity lowering control element 17. FIG. 14 is almost the same as FIG. 1 illustrated relative to Embodiment 1, but it is different from FIG. 11 as to that the output from the encode 20 is being sent to the velocity lowering control element 17. Once the operator directs to stop, the velocity lowering control element 17 controls the electric motor 15 and in addition, begins to monitor the velocity of the wheeled platform 1.

Figure 15:
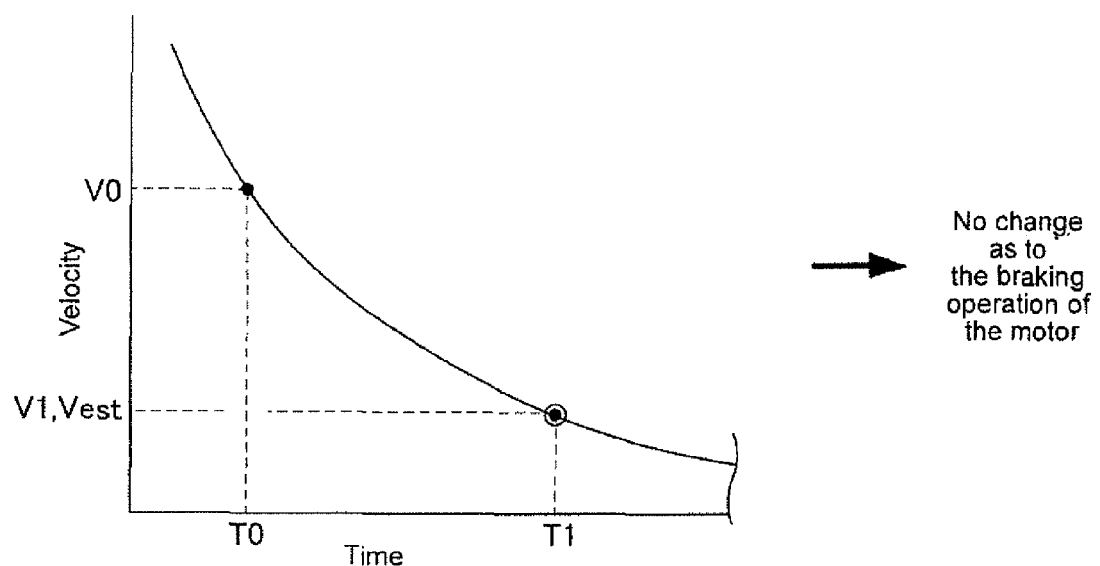
FIG. 15 is a schematic diagram illustrating a brake operation of Embodiment 2.

FIG. 15 is illustrating the state in that the velocity of the wheeled platform 1 decreases ideally by the braking due to the electric motor 15. The wheeled platform 1 having the initial velocity V0 at the beginning point T0 of decreasing velocity, which is the beginning point of decreasing velocity of the wheeled platform 1 by the velocity lowering control element 17, decrease the velocity to V1 at the time T1 and the velocity thereof coincides with the ideal velocity Vest at the point T1 expected from the time-course. Once the velocity lowering control element 17 confirms that the velocity of the wheeled platform 1 coincides with the ideal velocity Vest at the point T1, the brake method of the electric motor 15 will not be changed from the point T1 and the current control method as-is can be continuously used. It is considered that the specific circumstance in which the velocity of wheeled platform 1 decreases ideally is e.g., the case in that the stop direction is given when the wheeled platform 1 is passing the horizontal pathway.

Figure 16:
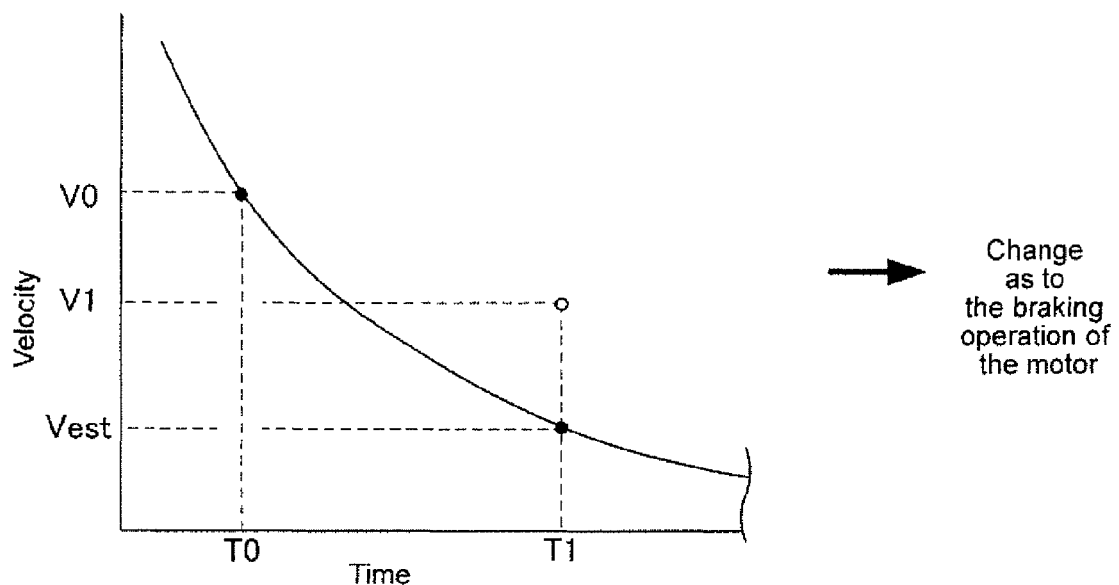
FIG. 16 is a schematic diagram illustrating a brake operation of Embodiment 2.

FIG. 16 is illustrating the state in that the velocity of the wheeled platform 1 decreases not ideally by braking due to the electric motor 15. The wheeled platform 1 having the initial velocity V0 at the beginning point T0 of decreasing velocity decrease the velocity to V1 at the time T1 but the velocity thereof is higher than the ideal velocity Vest at the point T1 expected from the time-course. The state at that the velocity decrease of the wheeled platform 1 is lower than the expected decrease after the velocity decrease of the wheeled platform 1 by the velocity lowering control element 17 begins is called as a short velocity decrease state.

When the velocity lowering control element 17 confirms that the velocity of the wheeled platform 1 does not coincide with the ideal velocity Vest at the point T1 and the wheeled platform 1 is in the short velocity decrease state, the brake method of the electric motor 15 will be changed from the point T1. It is considered that the specific circumstance in that the velocity of wheeled platform 1 does not decrease ideally is e.g., the case in that the stop direction is given when the wheeled platform 1 is passing the slope pathway. Particularly, in FIG. 16, the velocity of the wheeled platform 1 does not decrease sufficiently despite braking of the electric motor 15. This kind of incident takes place likely when the wheeled platform 1 is passing on the down slope.

Specifically, the velocity lowering control element 17 searches the initial velocity as the velocity of the wheeled platform 1 at the beginning point of the operation of the velocity lowering control element 17 from the time-course and recognizes the velocity level of the initial velocity relative to the time-course after a predetermined time is past, and when the actual velocity of the wheeled platform 1 after the predetermined time from the initial point T0 pasts (time point T1) is faster than the recognized velocity, it is decided that a short velocity decrease state takes place.

[Normal Operation of Velocity Lowering Control Element]

Next, the inventor sets forth that the velocity lowering control element 17 decides that the velocity decrease of the wheeled platform 1 is not ideal and how to change specifically the control of the electric motor 15. First of all, it is necessary to set forth how the electric motor 15 is controlled from the beginning of the velocity decrease of the wheeled platform 1 by the velocity lowering control element 17.

Figure 17:
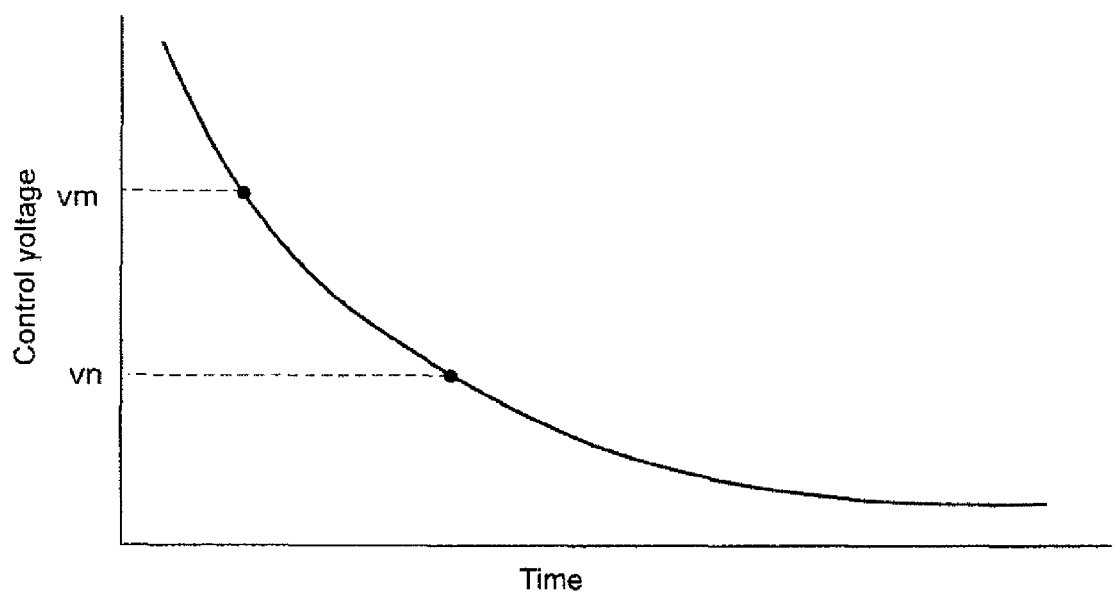
FIG. 17 is a schematic diagram illustrating a brake operation of Embodiment 2.

FIG. 17 is illustrating the control data related to the control voltage of the electric motor 15 and the time referred by the velocity lowering control element 17. The higher control voltage of the electric motor 15, the stronger the braking force to the wheeled platform 1 is given so that the velocity lowering control element 17 operative based on the control data gives the brake gradually weaken over time to the wheeled platform 1. According to such control, the velocity lowering control element 17 is operative to decrease the velocity of the wheeled platform 1 assuredly and quietly. Specifically, the velocity lowering control element 17 is changing the braking force to the wheeled platform 1 over time even in the normal sate set forth referring to FIG. 15.

Meantime, the velocity of the wheeled platform 1 changes depending on the pressure level of the bar 9 by the operator who tries to move the wheeled platform 1. Accordingly, the velocity of the wheeled platform 1 cannot be obtained right before until the operator directs to stop the wheeled platform and therefore must not be predicted in advance. It is suspected that the problem as to braking the wheeled platform 1 based on the control data illustrated in FIG. 17 takes place even though the velocity of the wheeled platform 1 being stopped should be different every stop-operation. Specifically, given the wheeled platform 1 is braked using the control data of FIG. 17, sometimes over braking takes place and other times short braking may take place. Conclusively speaking, the initial value of the control voltage is changed in accordance with the velocity of the moving wheeled platform 1 to be stopped so that the wheeled platform 1 can be braked appropriately.

Figure 18:
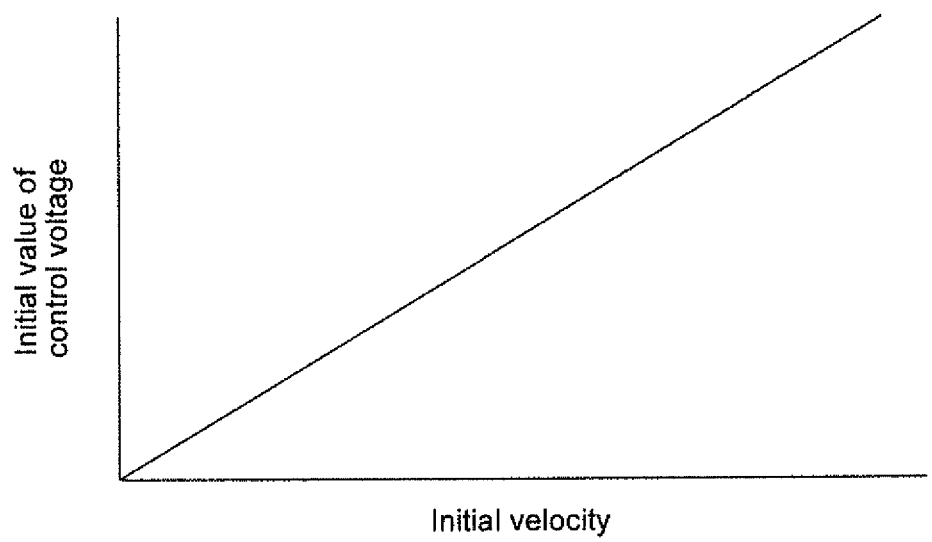
FIG. 18 is a schematic diagram illustrating a brake operation of Embodiment 2.

FIG. 18 is illustrating the data in that the initial velocity and the initial value of the control voltage are related. Referring to FIG. 18, the higher the initial velocity, the higher the initial value of the control voltage is set. Accordingly, when the initial velocity of the wheeled platform 1 is high, the velocity lowering control element 17 controls the control voltage of the electric motor 15 so as to lower while copying the graph of FIG. 17 over time as the initial value vm illustrated in the left side of FIG. 17. On the other hand, when the initial velocity of the wheeled platform 1 is low, the velocity lowering control element 17 controls the control voltage of the electric motor 15 so as to lower while copying the graph of FIG. 17 over time as the initial value vn illustrated in the right side of FIG. 17. Specifically, the time of the abscissa in FIG. 17 is relative and the position corresponding to the beginning of braking will change according to the velocity of the wheeled platform 1.

This is the normal operation of the velocity lowering control element 17 set forth as to Embodiment referring to FIG. 15. The velocity lowering control element 17 is operative in such mode so that the velocity of the wheeled platform 1 decreases as ideal and referring to FIG. 15, the velocity V1 of wheeled platform 1 at the time point T1 must be the same as Vest.

[Change of the Control Method of the Velocity Lowering Control Element]

Figure 19A:
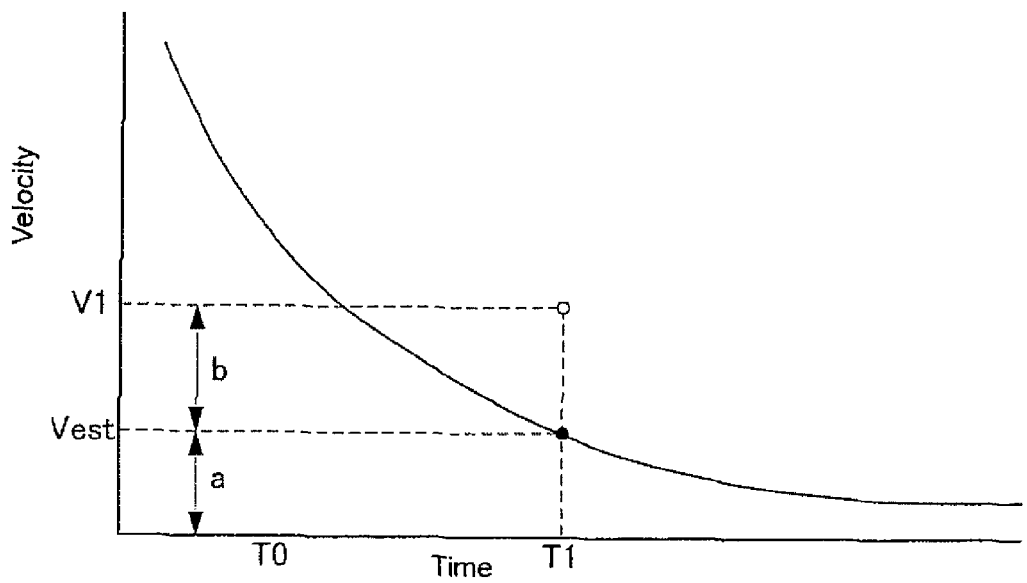
FIGS. 19(A) and 19(B) are schematic diagrams illustrating a brake operation of Embodiment 2.
Figure 19B:
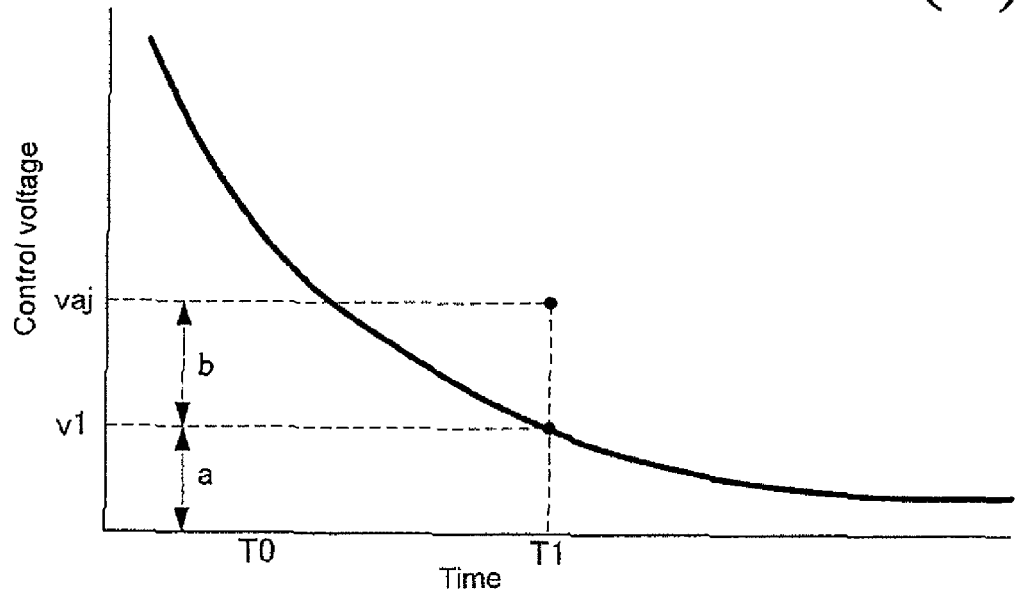

Next, the inventor sets forth the specific procedure relative to the velocity decrease of the wheeled platform 1 by the velocity lowering control element 17 when the velocity lowering control element 17 recognizes that the control method of the electric motor 15 needs to be changed as set forth referring to FIG. 16. The velocity lowering control element 17 calculates how much the velocity of the wheeled platform is out of the ideal velocity at the time point T1 when the necessity of the control method is recognized. As the specific method, referring to the time-course in FIG. 19(A), the ratio of the ideal velocity Vest and the actual velocity V1 shall be obtained. At this time, the ratio is a:b. Next, the velocity lowering control element 17 changes the control voltage (FIG. 19(B)) of the electric motor 15, which is v1 at the time T1, to the change value vaj referring to the above ratio. Specifically, the velocity lowering control element 17 obtains the change value vaj to make v1:aj=a:b and controls the electric motor 15 to be operative at the voltage of the change value vaj. According to the control voltage change, the wheeled platform 1 will receive a strong brake immediately after the time T1 and the wheeled platform 1 assuredly decreases the velocity thereof. In such aspect, according to the structure of Embodiment 1, the wheeled platform 1 will assuredly be braked due to the eclectic motor 15 even though the wheeled platform 1 is moving on the down slope. Accordingly, when the velocity lowering control element 17 finds the wheeled platform 1 in a short velocity decrease state, the velocity lowering control element 17 becomes operative to increase further the brake force of the electric motor 15.

Figure 20:
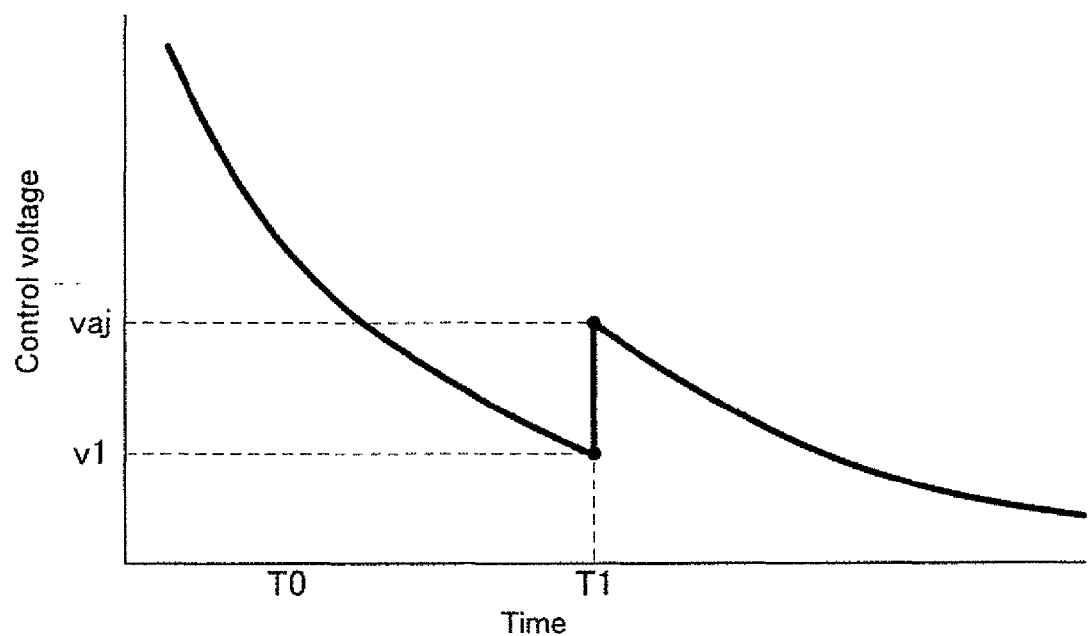
FIG. 20 is a schematic diagram illustrating a brake operation of Embodiment 2.

FIG. 20 is illustrating the aspect when the velocity lowering control element 17 changes the control method at the time T1. Referring to FIG. 20, the velocity lowering control element 17 is operative following the control data as set forth in FIG. 17 after the brake voltage of the electric motor 15 is increased up to the change value vaj at the time T1. Specifically, the velocity lowering control element 17 decreases the control voltage along with the graph of the control data from the change value vaj set as the beginning point on the control data.

The velocity lowering control element 17 repeatedly changes the control of the electric motor 15 based on the evaluation of the velocity of the wheeled platform 1 using the time-course as a benchmark as set forth above and the evaluation results thereof. Specifically, the velocity lowering control element 17 reviews the control of the electric motor 15 at 20 msec after the beginning of decreasing velocity T0 and repeats the review every 20 msec thereafter. When the velocity of the wheeled platform 1 becomes the set value Vconf, the brake control element 18 is operative as the same as Embodiment 1. According to this operation, the wheeled platform 1 will assuredly stop.

As set forth above, the structure of Embodiment 2 sets forth another Embodiment to solve the problem of the present invention. Specifically, according to the structure of Embodiment, a mobile radiation device that can be assuredly stopped on the horizontal pathway without jounce and can be stopped on the slope pathway in the short period of time can be provided. The rationale for that the device can be stopped without jounce on the horizontal pathway is based on the same structure as previously described for Embodiment 1.

Further, Embodiment 2 provides the idea in the case of moving on the slope pathway. This section is different from the previous structure. Specifically, the velocity lowering control element 17 is operative to increase the braking force of the electric motor 15 when the velocity decrease of the wheeled platform 1 after beginning of the operation is out of the time-course indicating the ideal change of the velocity of the wheeled platform 1. In some case, when the wheeled platform 1 moving on the slope is being stopped, the velocity decrease of the wheeled platform 1 may not be sufficient because of the short of the braking force of the electric motor 15. In such cases, according to the present invention, when the velocity decrease of the wheeled platform 1 is not ideal, the braking force of the electric motor 15 is enhanced so that the incident in which the wheeled platform 1 continues to move for a long time ignoring the direction of stop to the wheeled platform 1 moving on the slope can be restricted.

Given the velocity lowering control element 17 decides whether the velocity decrease of the wheeled platform 1 is short or not based on the time-course indicating ideal velocity decrease of the wheeled platform, the velocity lowering control element 17 assuredly can recognize the short of velocity decrease of the wheeled platform 1 and can be operative.

The present invention is not limited to the above structure and further following alternative Embodiment can be implemented.

(1) The above Embodiments are set forth as independent structure each other but the structure of Embodiment 2 may include the structure of Embodiment 1. In this case, given the velocity of the wheeled platform 1 increases after the operator directs to stop the wheeled platform through the brake lever 9b, the operation relative to the brake control element 18 of Embodiment 1 may structure-wise supersede the velocity lowering control element 17 of Embodiment 2. Further, given the velocity of the wheeled platform 1 increases after the operator directs to stop the wheeled platform through the brake lever 9b, and structure-wise if the velocity of the wheeled platform 1 at that time is higher than the certain constant velocity, the operation of Embodiment 1 may supersede and if the velocity of the wheeled platform 1 is lower than the certain constant velocity, the operation of Embodiment 2 may supersede.

INDUSTRIAL APPLICABILITY

As set forth above, the image processing device of the present invention is suitable for medicinal field.

| | Explanation of References |
|---|---|
| 1 | Wheeled platform |
| 3 | X-ray tube (Radiation source) |
| 4 | FPD (Detection means) |
| 9 | Bar |
| 9a | Pressure sensor |
| 9b | Brake lever (Stop direction input means) |
| 15 | Electric motor (Driving means) |
| 16 | Assist control element (Assist control means) |
| 17 | Velocity lowering control element (velocity lowering control means) |
| 18 | Brake control element (Brake control means) |
| 19 | Brake module |
| 20 | Encoder (Velocity measurement means) |
| 28 | Memory (Memory storage means) |

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A mobile radiation device, comprising:
   a wheeled platform, further comprising a radiation source operative to radiate a radiation during a use and a detector operative to detect the radiated radiation during said use and to output detected signals;
   a grip bar operative for gripping by an external user during the use while said wheeled platform is moving relative to a support surface and to detect a pressure applied by said external user during said use;
   a driving module that is operative to drive said wheeled platform;

a pressure sensor that is operative to detect the pressure added to said grip bar during the use;

an assist control module operatively drives said driving module during said use according to an output from said pressure sensor;

a velocity measurement module that operatively measures a move velocity of said wheeled platform;

a stop direction input module operative to determine and input a direction for stopping said wheeled platform from the operator during said use;

a brake module that operatively stops said wheeled platform that is moving during an engagement thereof;

a velocity lowering control module that operatively controls said driving module so as to add a braking force to lower the move velocity of said wheeled platform that is moving on a horizontal pathway prior to turning said brake module operative by inputting a direction from the operator into said stop direction input module, and a brake control module that is operative to stop said wheeled platform during said use by turning said brake module operative when the move velocity of said wheeled platform decreases until a predetermined velocity by said velocity lowering control module, wherein;

(A) said braking control module operatively turns said brake module operative when the velocity of said wheeled platform increases despite a beginning of a braking said wheeled platform by said velocity lowering control module.

2. A mobile radiation device, comprising:

a wheeled platform, further comprising a radiation source operative to radiate a radiation, a detector detects the radiated radiation and outputs detected signals;

a grip bar operative for gripping by an external user during a use while said wheeled platform is moving relative to a support surface and to detect a pressure applied by said external user during said use;

a driving module that is operative to drive said wheeled platform;

a pressure sensor that is operative to detect the pressure added to said grip bar during the use;

an assist control module operatively drives said driving module during said use according to an output from said pressure sensor;

a velocity measurement module that operatively measures a move velocity of said wheeled platform;

a stop direction input module operative to input a direction for stopping said wheeled platform from the operator;

a brake module operative to stop said wheeled platform that is moving;

a velocity lowering control module that operatively controls said driving means effective to add a braking force to lower the move velocity of said wheeled platform that is moving on a horizontal pathway prior to turning said brake module operative by inputting a direction from the operator into said stop direction input module, and a brake control means that stops said wheeled platform by turning said brake module operative when the velocity of said wheeled platform decreases until the predetermined velocity by said velocity lowering control means, wherein;

(B1) a memory module operatively stores a time-course of the velocity obtained by an actual measurement of the move velocity in advance when the velocity of said wheeled platform moving on the horizontal pathway is lowered by said velocity lowering control module; and (B2) said velocity lowering control module operatively strengthens the braking force of said driving module upon determining a short velocity decrease state, and wherein a velocity decrease of said wheeled platform after beginning of braking said wheeled platform is less than a decrease expected from said time-course.

3. A mobile radiation device comprising:

a wheeled platform, further comprising a radiation source operative to radiate a radiation during a use and a detector operative to detect the radiated radiation during said use and to output detected signals;

a grip bar operative for gripping by an external user during the use while said wheeled platform is moving relative to a support surface and to detect a pressure applied by said external user during said use;

a driving module that is operative to drive said wheeled platform;

a pressure sensor that is operative to detect the pressure added to said grip bar during the use;

an assist control module operatively drives said driving module during said use according to an output from said pressure sensor;

a velocity measurement module that operatively measures a move velocity of said wheeled platform;

a stop direction input module operative to determine and input a direction for stopping said wheeled platform from the operator during said use;

a brake module that operatively stops said wheeled platform that is moving during an engagement thereof;

a velocity lowering control module that operatively controls said driving module so as to add a braking force to lower the move velocity of said wheeled platform that is moving on a horizontal pathway prior to turning said brake module operative by inputting a direction from the operator into said stop direction input module, and a brake control module that is operative to stop said wheeled platform during said use by turning said brake module operative when the move velocity of said wheeled platform decreases until a predetermined velocity by said velocity lowering control module, wherein;

(A) said braking control module operatively turns said brake module operative when the velocity of said wheeled platform increases despite a beginning of a braking said wheeled platform by said velocity lowering control module; and (B1) a memory module operatively stores a time-course of the velocity obtained by an actual measurement of the move velocity in advance when the velocity of said wheeled platform moving on the horizontal pathway is lowered by said velocity lowering control module; and (B2) said velocity lowering control module operatively strengthens the braking force of said driving module upon determining a short velocity decrease state, and wherein a velocity decrease of said wheeled platform after beginning of braking said wheeled platform is less than a decrease expected from said time-course.

4. A mobile radiation device, according to claim 2, wherein:

the velocity lowering control module operatively (i) searches the initial velocity as the velocity of said wheeled platform at a beginning point of an operation of said velocity lowering control module from said time-course, (ii) recognizes a velocity level of the initial velocity relative to said time-course after the predetermined time is past, and (iii) when the actual velocity of said wheeled platform after the predetermined time from the initial point of the operation is higher than the recognized velocity, (iv) it is decided that said wheeled platform is in the short velocity decrease state.

5. A mobile radiation device, according to claim 3, wherein:

the velocity lowering control module operatively (i) searches the initial velocity as the velocity of said wheeled platform at a beginning point of an operation of said velocity lowering control module from said time-course, (ii) recognizes a velocity level of the initial velocity relative to said time-course after the predetermined time is past, and (iii) when the actual velocity of said wheeled platform after the predetermined time from the initial point of the operation is higher than the recognized velocity, (iv) it is decided that said wheeled platform is in the short velocity decrease state.

6. A mobile radiation device, according to claim 1, wherein:

said mobile radiation device is operative for rounding.

7. A mobile radiation device, according to claim 4, wherein:

said mobile radiation device is operative for rounding.

8. A mobile radiation device, according to claim 5, wherein:

said mobile radiation device is operative for rounding.

* * * * *